United States Patent [19]

LaMattina et al.

[11] 4,435,396

[45] Mar. 6, 1984

[54] ANTIULCER 2-GUANIDINO-4-(2-SUBSTITUTED-AMINO-4-IMIDAZOLYL)THIAZOLES AND PROCESS THEREFOR

[75] Inventors: John L. LaMattina, Ledyard; Christopher A. Lipinski, Waterford, both of Conn.

[73] Assignee: Pfizer Inc., New York, N.Y.

[21] Appl. No.: 376,486

[22] Filed: May 10, 1982

[51] Int. Cl.$^3$ ................ C07G 417/04; A61K 31/425
[52] U.S. Cl. ............................. 424/248.51; 424/263; 424/267; 424/270; 544/133; 546/276; 546/209; 548/193; 548/198
[58] Field of Search ............... 544/133; 546/209, 276; 548/193, 198; 424/248.51, 263, 267, 270

[56] References Cited

U.S. PATENT DOCUMENTS

| 3,519,637 | 7/1970 | Hoffer | 260/306.8 |
|---|---|---|---|
| 4,220,654 | 9/1980 | Bolhofer et al. | 424/273 R |
| 4,374,843 | 2/1983 | LaMattina et al. | 548/190 |

FOREIGN PATENT DOCUMENTS

| 3640 | 8/1979 | European Pat. Off. | |
| 50458 | 4/1982 | European Pat. Off. | 548/193 |

OTHER PUBLICATIONS

Cornforth and Cornforth, J. Chem. Soc., pp. 96–102 (1947).

*Primary Examiner*—Robert T. Bond
*Attorney, Agent, or Firm*—Charles J. Knuth; Albert E. Frost; Robert K. Blackwood

[57] ABSTRACT

Heretofore unavailable 2-guanidino-4-(2-substituted-amino-4-imidazolyl)thiazoles; a novel process therefor, also advantageous for the preparation of known antiulcer 2-guanidino-4-(2-substituted-amino-4-imidazolyl)-thiazoles; intermediate compounds therefor; and a method for treatment of ulcers in mammals therewith.

36 Claims, No Drawings

ANTIULCER 2-GUANIDINO-4-(2-SUBSTITUTED-AMINO-4-IMIDAZOLYL)THIAZOLES AND PROCESS THEREFOR

BACKGROUND OF THE INVENTION

The present invention relates to novel and heretofore unavailable 2-guanidino-4-(2-substituted-amino-4-imidazolyl)thiazoles; a novel process therefor, also having advantages in the preparation of known compounds which are lower homologs thereof; and intermediate compounds useful in this novel process. These compounds have activity as antisecretory agents, histamine-$H_2$ antagonists and/or inhibitors of ethanol-induced gastric ulceration in rats and so are useful in inhibiting (i.e., preventing and treating) peptic ulcers.

Chronic gastric and duodenal ulcers, together known as peptic ulcers, are a common ailment for which a variety of treatments, including dietary measures, drug therapy and surgery, may be employed, depending on the severity of the condition. Particularly valuable therapeutic agents useful for the treatment of gastric hyperacidity and peptic ulcers are the histamine-$H_2$ receptor antagonists, which act to block the action of the physiologically active compound histamine at the $H_2$-receptor sites in the animal body and to thereby inhibit the secretion of gastric acid. The determination that many of the present compounds will also inhibit ethanol-induced ulcers in rats, further reflects the clinical value of the present compounds in the inhibition of gastric ulcers.

Compounds of the present class, having the formula

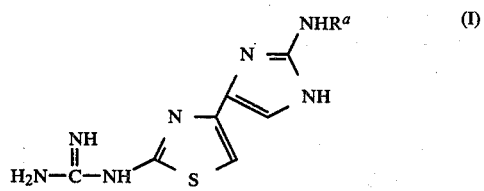

wherein $R^a$ is H, $(C_1-C_6)$alkyl, or $(C_7-C_{10})$phenylalkyl, said phenyl groups optionally monosubstituted with chloro, bromo, fluoro, $(C_1-C_3)$alkyl or $(C_1-C_3)$alkoxy, have been previously described as antiulcer agents, by dint of their antisecretory and histamine-$H_2$ antagonist activity. LaMattina and Lipinski, U.S. patent applications Ser. Nos. 196,231 filed Oct. 14, 1980, now abandoned, and 293,574, filed Aug. 20, 1981, now U.S. Pat. No. 4,374,843, issued Feb. 22, 1983 and corresponding to European Patent Application No. 50,458, published Apr. 28, 1982.

The novel process of the present invention is advantageous in the preparation of compounds of the formula (I), particularly when $R^a$ is $(C_3-C_6)$alkyl or $(C_7-C_{10})$phenylalkyl. Furthermore, the present process permits preparation of structurally related compounds of the formula (II), below, which are not available by the processes earlier disclosed in the above cited U.S. applications.

Key to the present process is the discovery that a primary or secondary amine will react with 2-amino-5-acetyloxazole, of the formula (IV) below, to form the intermediate 2-(substituted-amino)-5-acetylimidazole of the formula (V) below. Heretofore, no such reaction has been observed. The ring oxygen of 2-methyloxazole-4-carboxylic acid has been replaced with NH and then with $NC_6H_5$ under similar conditions with concommitant decarboxylation. Cornforth and Cornforth, J. Chem. Soc. 1947: 96–102.

SUMMARY OF THE INVENTION

The present invention relates to 2-guanidino-4-(2-amino-4-imidazolyl)thiazoles of the formula

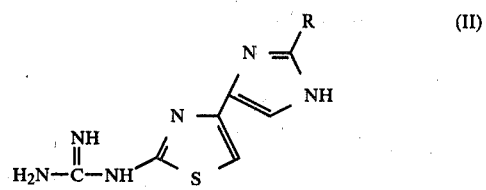

wherein
$R$ is $NHR^1$ or $NR^2R^3$;
$R^1$ is $(C_7-C_{12})$alkyl, $(C_6-C_{11})$pyridylalkyl, or $(C_{11}-C_{12})$phenylalkyl, optionally monosubstituted or disubstituted on the phenyl group with chloro, bromo, fluoro, $(C_1-C_3)$alkyl, $(C_1-C_3)$alkoxy or trifluoromethyl; and
$R^2$ and $R^3$ are each independently $(C_1-C_{12})$alkyl or $(C_7-C_{12})$phenylalkyl, optionally monosubstituted or disubstituted on the phenyl group with chloro, bromo, fluoro, $(C_1-C_3)$alkyl, $(C_1-C_3)$alkoxy or trifluoromethyl; or
$R^2$ and $R^3$ are taken together with the nitrogen to which they are attached to form a pyrrolidine, piperidine, perhydro-1H-azepine, or morpholine ring;
and the pharmaceutically-acceptable acid addition salt thereof.

The bracketed range of carbon atoms refers to the total number of carbon atoms in the group which follows. The carbon chain can be straight or branched; substituent groups such as phenyl can be substituted on any carbon on the chain. Pharmaceutically-acceptable acid addition salts are those with one or two equivalents of the acid. Suitable acids include, but are not limited to HCl, HBr, $H_2SO_4$, $H_3PO_4$, $CH_3SO_3H$, p-$CH_3C_6H_4SO_3H$, maleic acid, fumaric acid, succinic acid, and citric acid. For a current list of such salts, see Berge et al., J. Pharm. Sci. 66: 1–19, 1977.

Because of their facile preparation and high antisecretory activity, histamine-$H_2$ antagonist activity, and/or inhibition of ethanol-induced ulcers, preferred compounds of the formula (I) are as follows:

(1) when R is $NHR^1$ and $R^1$ is $(C_7-C_{12})$alkyl, the preferred values of $R^1$ are n-$C_7H_{15}$, n-$C_8H_{17}$ and n-$C_9H_{19}$;

(2) when R is $NHR^1$ and $R^1$ is $(C_6-C_{11})$pyridylalkyl, the preferred value of $R^1$ is 2-(2-pyridyl)-ethyl;

(3) when R is $NHR^1$ and $R^1$ is $(C_{11}-C_{12})$phenylalkyl (the phenyl group optionally substituted), the preferred value of $R^1$ is 5-phenyl-1-pentyl; and (4) when R is $NR^2R^3$, the preferred value is piperidino.

The present invention further relates to pharmaceutical compositions comprising an inert carrier and a compound of the formula (II) and a method of inhibiting gastric ulcers in a mammal by treatment with a compound of the formula (II).

The present invention relates also to a process for the preparation of compounds of the formula

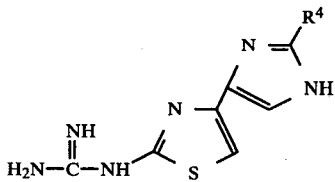

wherein $R^4$ is $NHR^5$ or $NR^2R^3$;

$R^5$ is $(C_1-C_{12})$alkyl, $(C_3-C_8)$cycloalkyl, $(C_6-C_{11})$-pyridylalkyl or $(C_7-C_{12})$phenylalkyl, optionally monosubstituted or disubstituted on the phenyl group with chloro, bromo, fluoro, $(C_1-C_3)$alkyl, $(C_1-C_3)$alkoxy or trifluoromethyl; and $R^2$ and $R^3$ are each independently $(C_1-C_{12})$alkyl or $(C_7-C_{12})$phenylalkyl, optionally monosubstituted or disubstituted on the phenyl group with chloro, bromo, fluoro, $(C_1-C_3)$alkyl, $(C_1-C_3)$alkoxy or trifluoromethyl; or $R^2$ and $R^3$ are taken together with the nitrogen to which they are attached to form a pyrrolidine, piperidine, perhydro-1H-azepine, or morpholine ring. The overall process comprises the following chemical steps:

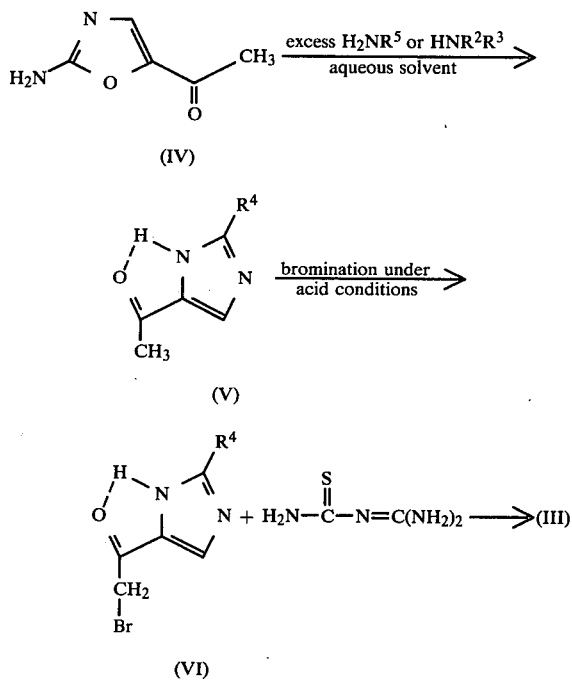

It is preferred to isolate the product (III) directly from the reaction mixture as the monohydrobromide salt, which, if desired, can be converted to the free base or to an alternative pharmaceutically-acceptable salt, such as the dihydrochloride.

Also encompassed by the present invention are the intermediates of the formulae (V) and (VI), and, specifically, the monohydrobromide salts of the compounds of formula (III), said salts having unexpected advantage in the initial isolation of the products of the formula (III).

Because operation of the present process is particularly facile, and because the resulting products have particularly high antisecretory, histamine-$H_2$ antagonist and/or ethanol-induced ulcer inhibitory activity, the preferred values of $R^4$ in the above process and intermediates are as follows:

(1) when $R^4$ is $NHR^5$, and $R^5$ is $(C_1-C_{12})$alkyl, preferred values of $R^5$ are n-$C_6H_{13}$, n-$C_7H_{15}$, n-$C_8H_{17}$ and n-$C_9H_{19}$;

(2) when $R^4$ is $NHR^5$ and $R^5$ is $(C_3-C_8)$cycloalkyl, the preferred value of $R^5$ is cyclopropyl;

(3) when $R^4$ is $NHR^5$ and $R^5$ is $(C_6-C_{11})$pyridylalkyl, the preferred value of $R^5$ is 2-(2-pyridyl)-ethyl;

(4) when $R^4$ is $NHR^5$ and $R^5$ is $(C_7-C_{12})$phenylalkyl, optionally mono- or disubstituted on phenyl, the preferred values of $R^5$ are 2-(p-chlorophenyl)-ethyl, 3-phenyl-1-propyl, 4-phenyl-1-butyl or 5-phenyl-1-pentyl;

(5) when $R^4$ is $NR^2R^3$, the preferred value is piperidino.

DETAILED DESCRIPTION OF THE INVENTION

The compounds of the formula (III), which encompasses compounds of the formulae (I) and (II), are readily prepared by operation of the process of the present invention, as outlined in the above chemical steps: (IV)→(V)→(VI)→(III).

The first step, (IV)→(V), is carried out in the presence of an excess amine reactant in an aqueous solvent. When the reactants dissolve under the reaction conditions, the preferred solvent is water alone. When there is incomplete solubility of the reactants under the reaction conditions, a polar, water-miscible, reaction-inert, organic solvent is added. As used herein, a "reaction-inert solvent" is one which does not interact with reagents, intermediates or products in a manner which adversely effects the yield of the desired product. In the present instance, ethers such as tetrahydrofuran or lower, preferably branched, alcohols, are well suited. The preferred organic solvent, when one is required to achieve solubility, is isopropanol. The reaction is readily monitored by standard methods of thin layer chromatography (tlc) well-known in the art, for example using silica gel plates with chloroform containing 1-10% methanol as eluant. The reaction is generally continued until the starting aminooxazole is no longer detected by tlc, thereby simplifying the isolation of pure intermediate. The reaction can be carried out over a wide range of temperature, e.g., 50°-150° C., under pressure if necessary. Conveniently, the reaction is carried out at the reflux temperature of the reaction mixture (50°-100° C.), depending upon the boiling point of the aqueous amine or combined aqueous amine and organic solvent. The intermediate compounds (V) are usually isolated by evaporation and purified by column chromatography. If desired, the product is further purified by recrystallization from an organic solvent such as acetonitrile, toluene or cyclohexane.

The second step of the overall sequence, (V)→(VI) is acid catalyzed bromination of the methyl group in (V) which is activated by a carbonyl. While a variety of standard brominating agents can be used in this reaction, the preferred reagent is bromine itself. The preferred acid, also conveniently used as solvent, is concentrated hydrobromic acid. The intermediate (VI) is readily isolated in the form of its water insoluble free base by concentration and neutralization with an aqueous base.

The third step of the overall sequence, (VI)→(III), involves condensation of the compound of the formula (VI) with substantially one molar equivalent of amidinothiourea. The reaction is carried out in a reaction-inert organic solvent such as tetrahydrofuran, a lower alcohol such as methanol, ethanol or isopropanol, or a lower ketone such as acetone or methyl ethyl ketone. Acetone is a preferred solvent, since product precipitates cleanly as the monohydrobromide salt from this solvent and is therefore readily recovered in high yield by simple filtration. The hydrobromide salt is readily converted to free base by standard neutralization/extraction methods. To obtain other pharmaceutically-acceptable salts, the free base is dissolved in an organic solvent and either one equivalent or at least two equivalents of the acid corresponding to the desired salt is added. The salt is recovered by filtration, concentration or addition of a non-solvent, or by a combination of these steps. The preferred salt is the dihydrochloride, readily precipitated from a methanol solution of the free base by diffusion of the solution with an excess of anhydrous hydrogen chloride.

The 5-acetyl-2-aminooxazole required for the present process is a known compound. Kochetikov et al., Chemical Abstracts 54: 14230h (1960). A preferred preparative method is exemplified below. Amidinothiourea and the amines also required for the present process are available commercially or by literature methods.

For example, 2-aminoheptane is available from 2-heptanone by reduction of the oxime, reductive amination or the Leukart reaction, Rohrmann and Schonle, J. Am. Chem. Soc. 70: 2811 (1948); 2-methyl-1-aminocyclohexane is available from Hoffmann degradation of 2-methylcyclohexane-1-carboxamide, Gutt. Ber. 40: 2061 (1907); N-ethyl-2-phenyl-2-propylamine is available by reductive amination, Woodruff et al., J. Am. Chem. Soc. 62: 922 (1940); and 2-(3-pyridyl)-2-propylamine is prepared by the Leukart reaction, Burger and Walters, ibid, 72: 1988 (1950).

The antiulcer utility of the compounds of the formula (III) in mammals, including man, is reflected in their antisecretory, histamine-$H_2$ antagonist and/or inhibition of ethanol-induced ulcers in rats, as detailed in the Examples below. To inhibit (prevent or treat) gastric ulcers in a mammalian subject, the products of the present invention are administered by a variety of conventional routes of administration including orally and parenterally. Preferably, the compounds are administered orally. In general, these compounds will be administered orally at doses between about 0.1 and 20 mg/kg body weight of the subject to be treated per day, preferably from about 0.2 to 2.5 mg/kg per day, in single or divided doses. If parenteral administration is desired, then these compounds can be given at total daily doses between about 0.1 and 1.0 mg/kg body weight of the subject to be treated. However, at the discretion of the attending physician, some variation in dosage will necessarily occur, depending upon the condition of the subject being treated and the particular compound employed.

The compound is administered alone or in combination with pharmaceutically-acceptable carriers or diluents, in either single or multiple doses. Suitable pharmaceutical carriers include inert diluents or fillers, sterile aqueous solutions and various organic solvents. The pharmaceutical compositions formed by combining the novel compounds of formula I or salts thereof and pharamceutically acceptable carriers are readily administered in a variety of dosage forms such as tablets, powders, capsules, lozenges, syrups and the like. These pharmaceutical compositions can, if desired, contain additional ingredients such as flavorings, binders, excipients and the like. Thus, for oral administration, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials therefor include lactose or milk sugar and high molecular weight polyethylene glycols. When aqueous suspensions or elixirs are desired for oral administration, the essential active ingredient therein may be combined with various sweetening or flavoring agents, coloring matters or dyes and, if desired, emulsifying agents or suspending agents, together with diluents such as water, ethanol, propylene glycol, glycerin, or combinations thereof.

Preferably, the products of this invention are administered orally in unit dosage form, i.e. as a single physically discrete dosage unit containing an appropriate amount of the active compound in combination with a pharmaceutically acceptable carrier or diluent. Examples of such unit dosage forms are tablets or capsules, containing from about 5 to 1,000 mg of the active ingredient, the compound of formula (III) comprising from about 10% to 90% of the total weight of the dosage unit.

For parenteral administration, solutions or suspensions of the compounds of formula (III) in sterile aqueous solutions, for example aqueous propylene glycol, sodium chloride, dextrose or sodium bicarbonate solutions are employed. Such dosage forms are suitably buffered if desired. The preparation of suitable sterile liquid media for parenteral administration will be well known to those skilled in the art.

The present invention is illustrated by the following examples. However, it should be understood that the invention is not limited to the specific details of these examples. All temperatures are in degrees centigrade.

EXAMPLE 1

5-Acetyl-2-Aminooxazole (IV)

A mixture of 132.3 g (0.80 m) of 2-bromo-1-hydroxy-3-oxo-1-butene, 120.1 g (2.0 m) of urea, and 1.85 l of acetone was heated at reflux with overhead stirring for one hour. The mixture was concentrated and the oil residue was taken up into 600 ml of water, then made basic with concentrated ammonium hydroxide. After sitting at room temperature for 0.5 hour, a precipitate formed. This was collected, and dried in vacuo to give 61.1 g of crude product. The filtrate was again concentrated and the oil residue taken up in 50 ml of water and again made basic with concentrated ammonium hydroxide. After sitting overnight a second crop of crude product, amounting to 17.6 g was isolated. Both crops were combined and recrystallized from methanol to give 50.3 g (50%) of 5-acetyl-2-aminooxazole, m.p. 214°–215°.

EXAMPLE 2

General Procedure of 2-Substituted-Amino-5-Acetylimidazoles (V)

A mixture of 2.0 g (16 mmol) of 5-acetyl-2-aminooxazole, 20 ml of the appropriate amine and 30 ml of water was heated at reflux for 3 to 96 hours, as indicated below (in the case of some lipophilic amines, isopropanol was added as necessary to obtain a homogeneous reaction mixture). The mixture was concentrated (distilled, if necessary, to remove all traces of the amine) and the residue then chromatographed over 60 g of silica gel, using 4:1 ethyl acetate/hexane as eluant. Once all of the less polar material (pyrimidine by-product) was eluted, the column was eluted with 19:1 chloroform/methanol in order to obtain the more polar imidazole product. Analytically pure imidazole was obtained by recrystallization from the appropriate solvent as detailed below. In this manner, the following 2-substituted-amino-5-acetylimidazoles were prepared:

| Substituted Amino Group ($R^4$) | Reaction Time (Hours) | Yield (IV)→(V) | mp | Recrystallization Solvent |
| --- | --- | --- | --- | --- |
| $CH_3NH$ | 16 | 52% | 195–196° | $CH_3CN$ |
| $C_2H_5NH$ | 4 | 52% | 198–200° | $CH_3CN$ |
| $CH_3(CH_2)_2NH$ | 18 | 43% | 215–216° | $CH_3CN$ |
| $CH_3(CH_2)_3NH$ | 24 | 58% | 175–177° | $CH_3CN$ |
| $CH_3(CH_2)_4NH$ | 3 | 23% | 168–170° | $CH_3CN$ |
| $CH_3(CH_2)_5NH$ | 4 | 43% | 161–162° | $CH_3CN$ |
| $CH_3(CH_2)_6NH$ | 20 | 39% | 155–156° | $CHCl_3$ |
| $CH_3(CH_2)_7NH$ | 20 | 58% | 145–148° | toluene |
| $CH_3(CH_2)_8NH$ | 20 | 39% | 145–146° | toluene |
| $CH_3(CH_2)_9NH$ | 20 | 81% | 140–142° | cyclohexane |
| $(CH_3)_2CHNH$ | 96 | 38% | 214–215° | $CH_3CN$ |
| $C_2H_5(CH_3)CHNH$ | 60 | 27% | 194–196° | $CH_3CN$ |
| $(CH_3)_2CH(CH_2)_2NH$ | 6 | 58% | 188–190° | $CH_3CN$ |
| cyclopropylamino | 22 | 37% | 138–140° | $CH_3CN$ |
| cyclopentylamino | 5 | 33% | 229–232° | $CH_3CN$ |
| cyclohexylamino | 24 | 44% | 249–251° | $CH_3CN$ |
| $C_6H_5CH_2NH$ | 3 | 43% | 200–202° | $CH_3CN$ |
| $C_6H_5(CH_2)_2NH$ | 7 | 35% | 193–194° | $CH_3CN$ |
| $C_6H_5(CH_2)_3NH$ | 9 | 33% | 185–186° | $CH_3CN$ |
| $C_6H_5(CH_2)_4NH$ | 23 | 58% | 170–173° | $CH_3CN$ |
| 2-(4-pyridyl)ethylamino | 3 | 41% | 232–234° | $CH_3CN$ |
| 2-(2-pyridyl)ethylamino | 4 | 47% | 171–174° | $CH_3CN$ |
| 4-chlorophenethylamino | 4 | 39% | 213–214° | $CH_3CN$ |
| $(CH_3)_2N$ | 4 | 45% | 181–183° | toluene |
| $C_2H_5(CH_3)N$ | 6 | 50% | 127–128° | cyclohexane |
| $(C_2H_5)_2N$ | 96 | 23% | 103–104° | hexane |
| morpholino | 4 | 46% | 220–222° | $CH_3CN$ |
| pyrrolidino | 2 | 48% | 230–232° | $CH_3CN$ |
| piperidino | 5 | 32% | 133–135° | cyclohexane |

EXAMPLE 3

General Procedure for 2-Substituted-Amino-5-(2-Bromoacetyl)imidazoles (VI)

A solution of 1.0 g of the appropriate ketone in 25 ml of concentrated hydrobromic acid was stirred at room temperature and a 5% molar excess of bromine was added dropwise over a two minute period. The mixture was then heated at 80° (external) for one hour, during which time the bromine color dissipated. The mixture was cooled, then concentrated. The residue was triturated with saturated sodium bicarbonate solution and the precipitate which formed from this basic medium was collected, washed with water, then dried in vacuo to afford the following 2-amino-5-(2-bromoacetyl)imidazoles as solids which were characterized by nmr spectroscopy in DMSO-$d_6$, unless otherwise specified:

| Substituted Amino Group ($R^4$) | Yield (V→VI) | nmr (delta, ppm) |
| --- | --- | --- |
| $CH_3NH$ | 70% | 7.73 (s, 1H), 6.47 (b, 1H), 4.57 (s, 2H), 2.78 (d, 3H) |
| $C_2H_5NH$ | 74% | 7.73 (s, 1H), 6.52 (b, 1H), 4.34 (s, 2H), 3.24 (p, 2H), 1.10 (t, 3H) |
| $CH_3(CH_2)_2NH$ | 77% | 7.69 (s, 1H), 6.55 (b, 1H), 4.33 (s, 2H), 3.15 (q, 2H), 1.50 (m, 2H), 0.87 (t, 3H) |
| $CH_3(CH_2)_3NH$ | 91% | 7.88 (s, 1H), 7.0 (b, 1H), 4.43 (s, 2H), 3.27 (m, 2H), 1.43 (m, 4H), 0.87 (t, 3H) |
| $CH_3(CH_2)_4NH$ | 85% | 7.67 (s, 1H), 6.5 (b, 1H), 4.27 (s, 2H), 3.28 (m, 2H), 1.38 (m, 6H), 0.91 (t, 3H) |
| $CH_3(CH_2)_5NH$ | 75% | 7.65 (s, 1H), 6.5 (b, 1H), 4.32 (s, 2H), 3.17 (m, 2H), 1.31 (m, 8H), 0.83 (t, 3H) |
| $CH_3(CH_2)_6NH$ | 97% | 8.23 (s, 1H), 4.56 (s, 2H), 3.30 (m, 2H), 1.21 (bs, 10H), 0.80 (t, 3H) |
| $CH_3(CH_2)_7NH$ | 98% | 8.22 (s, 1H), 4.49 (s, 2H), 3.26 (m, 2H), 1.22 (bs, 12H), 0.84 (t, 3H) |
| $CH_3(CH_2)_8NH$ | 90% | 8.23 (s, 1H), 4.58 (s, 2H), 3.27 (m, 2H), 1.27 (bs, 14H), 0.80 (t, 3H) |
| $CH_3(CH_2)_9NH$ | 99% | 8.06 (s, 1H), 4.46 (s, 2H), 3.20 (b, 2H), 1.26 (bs, 16H), 0.80 (t, 3H) |
| $(CH_3)_2CHNH$ | 63% | 7.75 (s, 1H), 6.43 (bd, 1H), 4.38 (s, 2H), 3.90 (m, 1H), 1.19 (d, 6H) |
| $C_2H_5(CH_3)CHNH$ | 60% | 7.50 (s, 1H), 5.4 (b, 1H), 4.11 (s, 2H), 3.75 (m, 1H), 1.48 (m, 2H), 1.12 (d, 3H), 0.90 (t, 3H) |
| $(CH_3)_2CH(CH_2)_2NH$ | 80% | 7.87 (s, 1H), 6.9 (b, 1H), 4.42 (s, 2H), 3.28 (m, 2H), 1.9–1.3 (m, 3H), 0.92 (d, 6H) |
| cyclopropylamino | 45% | 7.94 (s, 1H), 5.4 (b, 1H), 4.47 (s, 2H), 0.9–0.4 (b, 5H) |
| cyclopentylamino | 81% | 7.97 (s, 1H), 7.0 (b, 1H), 4.46 (s, 2H), 4.1 (b, 1H), 2.0–1.4 (b, 8H) |
| cyclohexylamino | 83% | 7.87 (s, 1H), 6.9 (b, 1H), 4.42 (s, 2H), 3.5 (b, 1H), 2.0–1.0 (m, 10H) |
| $C_6H_5CH_2NH$ | 92% | 7.95 (s, 1H), 7.8 (b, 1H), 7.15 (s, 5H), 4.5 (s and d, 4H) |
| $C_6H_5(CH_2)_2NH$ | 84% | 7.73 (s, 1H), 7.23 (s, 5H), 6.53 (b, 1H), 4.36 (s, 2H), 3.42 (t, 2H), 2.80 (t, 2H) |
| $C_6H_5(CH_2)_3NH$ | 76% | 7.67 (s, 1H), 7.20 (s, 5H), 6.64 (b, 1H), 4.37 (s, 2H), 3.18 (t, 2H), 2.60 (t, 2H), 1.83 (m, 2H) |
| $C_6H_5(CH_2)_4NH$ | 75% | 7.79 (s, 1H), 7.37 (s, 5H), 6.77 (b, 1H), 4.42 (s, 2H), 3.33 (m, 2H), 1.9–1.6 (m, 6H) |
| 2-(4-pyridyl)ethylamino | 91% | 8.45 (d, 2H), 7.72 (s, 1H), 7.23 (d, 1H), 6.6 (b, 1H), 4.38 (s, 2H), 3.56 (m, 2H), 2.85 (t, 2H) |
| 2-(2-pyridyl)ethylamino | 94% | 8.43 (d, 1H), 7.95–7.6 (s and m, 2H), 7.4–7.2 (m, 2H), 6.75 (b, 1H), 4.34 (s, 2H), 3.60 (m, 2H), 2.97 (t, 2H) |
| 4-chlorophenethylamino | 100% | 7.76 (s, 1H), 7.27 (s, 5H), 6.73 (b, 1H), 4.37 (s, 2H), 3.48 (m, 2H), 2.77 (t, 2H) |
| $(CH_3)_2N$ | 52% | [$CDCl_3$] - 7.64 (s, 1H), 4.13 (s, 2H), 3.20 (s, 6H) |
| $(C_2H_5)CH_3N$ | 60% | 7.63 (s, 1H), 4.23 (s, 2H), |

-continued

| Substituted Amino Group ($R^4$) | Yield (V→VI) | nmr (delta, ppm) |
|---|---|---|
| ($C_2H_5$)$_2$N | 62% | 3.29 (q, 2H), 2.86 (s, 3H), 0.93 (t, 3H) 7.87 (s, 1H), 4.42 (s, 2H), 3.50 (q, 4H), 1.13 (t, 6H) |
| morpholino | 100% | 7.83 (s, 1H), 4.41 (s, 2H), 4.0–3.3 (m, 8H) |
| pyrrolidino | 47% | 7.81 (s, 1H), 4.37 (s, 2H), 3.40 (m, 4H), 1.89 (m, 4H) |
| piperidino | 71% | 7.70 (s, 1H), 4.28 (s, 2H), 3.3 (b, 4H), 1.4 (b, 6H) |

EXAMPLE 4

General Procedure for
2-Guanidino-4-(2-Substituted-Amino-4-imidazolyl)-thiazole Hydrobromides (III.HBr)

A mixture of 1 g of a bromoacetylimidazole of the preceding Example, an equimolar amount of amidinothiourea, and 50 ml of acetone was heated at reflux for one hour, during which time the product precipitated as its monohydrobromide salt. This solid was collected, washed with acetone, then dried in vacuo. It was then converted to its dihydrochloride salt as outlined in Example 5.

EXAMPLE 5

General Procedure for
2-Guanidino-4-(2-Substituted-Amino-4-imidazolyl)-thiazole Dihydrochlorides [III.(HCl)$_2$]

The hydrobromide salt was stirred in 50 ml of saturated NaHCO$_3$ solution for 15–30 minutes. The solid, now as the free base, was collected, washed with water, then dried in vacuo. This solid was taken up into a minimum amount of methanol. The methanol solution was saturated with HCl gas, then slowly diluted with ether. The resulting precipitate was collected, washed with ether, then dried in vacuo to give the dihydrochloride salt which was characterized by combustion analysis and/or spectral data as follows:

| No. | Substituent Amino Group ($R^4$) | Yield* (VI)→(III) | mp | Microanalysis/nmr |
|---|---|---|---|---|
| a | CH$_3$NH | 74% | >280° | Anal. Calcd. for C$_8$H$_{11}$N$_7$S.2HCl.H$_2$O: C, 29.27; H, 4.60; N, 29.87; S, 9.77. Found: C, 29.21; H, 4.14; N, 29.33; S, 9.17 |
| b | C$_2$H$_5$NH | 80% | 275° | Anal. Calcd. for C$_9$H$_{13}$N$_7$S.2HCl: C, 33.34; H, 4.66; N, 30.24; S, 9.89. Found: C, 32.93; H, 5.11; N, 29.39; S, 9.64 |
| c | CH$_3$(CH$_2$)$_2$NH | 59% | 227–229° | Anal. Calcd. for C$_{10}$H$_{15}$N$_7$S.2HCl: C, 35.50; H, 5.07; N, 28.99; S, 9.48. Found: C, 35.28; H, 5.14; N, 28.37; S, 9.42 |
| d | CH$_3$(CH$_2$)$_3$NH | 63% | 240° | Anal. Calcd. for C$_{11}$H$_{17}$N$_7$S.2HCl: C, 37.50; H, 5.43; N, 27.83; S, 9.10. Found: C, 37.44; H 5.48; N, 26.53; S, 8.34 |
| e | CH$_3$(CH$_2$)$_4$NH | 40% | 212–214° | Anal. Calcd. for C$_{12}$H$_{19}$N$_7$S.2HCl.H$_2$O: C, 37.49; H, 6.03; N, 25.51; S, 8.34. Found, C, 37.71; H, 5.71; N, 23.86; S, 7.80 |
| f | CH$_3$(CH$_2$)$_5$NH | 36% | >280° | Anal. Calcd. for C$_{13}$H$_{21}$N$_7$S.2HCl.H$_2$O: C, 39.20; H, 6.33; N, 24.61; S, 8.05. Found: C, 39.84; H, 5.86; N, 24.60; S, 8.19 |
| g | CH$_3$(CH$_2$)$_6$NH | 23% | >275° | Anal. Calcd. for C$_{14}$H$_{21}$N$_7$S.2HCl.H$_2$O: C, 40.78; H, 6.60; N, 23.78; S, 7.78. Found: C, 40.27; H, 6.13; N, 23.20; S, 7.72 |
| h | CH$_3$(CH$_2$)$_7$NH | 55% | >275° | nmr (DMSO-d$_6$), delta (ppm): 8.47 (b, 4H); 8.09 (b, 1H); 7.93 (s, 1H); 7.80 (s, 1H); 3.50 (b, 2H); 1.9–1.1 (b, 12H); 0.92 (t, 3H) |
| i | CH$_3$(CH$_2$)$_8$NH | 43% | >275° | Anal. Calcd. for C$_{16}$H$_{25}$N$_7$S.2HCl.H$_2$O: C, 43.63; H, 7.09; N, 22.26; S, 7.28. Found: C, 43.73; H, 6.48; N, 21.60; S, |

-continued

| No. | Substituent Amino Group (R⁴) | Yield* (VI)→(III) | mp | Microanalysis/nmr |
|---|---|---|---|---|
| j | CH₃(CH₂)₉NH | 9% | >275° | 7.04 nmr (DMSO-d₆), delta (ppm): 8.47 (b, 4H); 8.06 (b, 1H); 7.93 (s, 1H); 7.77 (s, 1H); 3.46 (b, 2H); 1.9–1.1 (b, 16H); 0.90 (t, 3H) |
| k | (CH₃)₂CHNH | 42% | 207–210° | nmr (DMSO-d₆), delta (ppm): 8.38 (b, 4H); 8.00 (b, 1H); 7.89 (s, 1H); 7.67 (s, 1H); 3.9 (b, 1H); 1.26 (d, 6H) |
| l | C₂H₅(CH₃)CHNH | 60% | 293–294° | nmr (DMSO-d₆), delta (ppm): 8.37 (b, 4H); 7.90 (s, 1H); 7.80 (b, 1H); 7.66 (s, 1H); 4.0 (b, 1H); 1.56 (m, 2H); 1.23 (d, 3H); 0.98 (t, 3H) |
| m | (CH₃)₂CH(CH₂)₂NH | 18% | >275° | Anal. Calcd. for C₁₂H₁₉N₇S.2HCl.H₂O: C, 37.50; H, 6.03; N, 25.51; S, 8.34. Found: C, 37.83; H, 5.75; N, 25.17; S, 8.00 |
| n | cyclopropylamino | 42% | >275° | Anal. Calcd. for C₁₀H₁₃N₇S.2HCl: C, 35.72; H, 4.50; S, 9.53. Found: C, 35.91; H, 4.81; S, 8.60 |
| o | cyclopentylamino | 21% | >275° | Anal. Calcd. for C₁₂H₁₇N₇S.2HCl.H₂O: C, 37.70; H, 5.54; N, 25.65; S, 8.38. Found: C, 37.28; H, 5.30; N, 24.89; S, 8.08 |
| p | cyclohexylamino | 38% | >275° | nmr (DMSO-d₆), delta (ppm): 8.19 (b, 4H); 7.80 (b, 1H); 7.67 (s, 1H); 7.48 (s, 1H); 3.4 (m, 1H); 1.9–1.0 (b, 10H) |
| q | C₆H₅CH₂NH | 40% | >275° | Anal. Calcd. for C₁₄H₁₅N₇S.2HCl: C, 43.53; H, 4.44; N, 25.38; S, 8.30. Found: C, 42.95; H, 4.75; N, 24.59; S, 8.25 |
| r | C₆H₅(CH₂)₂NH | 58% | >275° | nmr (DMSO-d₆), delta (ppm): 8.40 (b, 4H); 8.04 (b, 1H); 7.83 (s, 1H); 7.69 (s, 1H); 7.30 (s, 5H); 3.7 (b, 2H); 2.91 (t, 2H) |
| s | C₆H₅(CH₂)₃NH | 53% | 253–255° | Anal. Calcd. for C₁₆H₁₉N₇S.2HCl.H₂O: C, 44.44; H, 4.90; N, 22.67; S, 7.42. Found: C, 44.00; H, 4.64; N, 21.83; S, 7.14 |
| t | C₆H₅(CH₂)₄NH | 44% | 269–270° | nmr (DMSO-d₆), delta (ppm): 8.41 (b, 4H); 8.08 (b, 1H); 7.86 (s, 1H); 7.70 (s, 1H); 7.14 (s, 5H); 3.5 (b, 2H); 2.66 (m, 2H); 1.9–1.5 (b, 4H) |
| u | 2-(4-pyridyl)-ethylamino | 48% | 195° | nmr (DMSO-d₆), delta (ppm): 8.89 (d, 2H); 8.43 (b, 4H); 8.17 (d, 2H); 7.98 (s, 1H); 7.73 (s, 1H); 4.0 (b, 2H); 3.36 (m, 2H) |
| v | 2-(2-pyridyl)-ethylamino | 52% | 205–209° | Anal. Calcd. for C₁₄H₁₆N₈S.3HCl: C, 38.41; H, 4.37; N, 25.60; S, 7.32. Found: C, 38.38; H, 4.65; N, 24.78; S, 7.08 |
| w | 4-chlorophen-ethylamino | 60% | 275° | Anal. Calcd. for C₁₅H₁₆N₇SCl.2HCl.½H₂O: C, 40.60; H, 4.32; N, |

-continued

| No. | Substituent Amino Group ($R^4$) | Yield* (VI)→(III) | mp | Microanalysis/nmr |
|---|---|---|---|---|
| x | $(CH_3)_2N$ | 66% | >285° | 22.09; S, 7.23. Found: C, 40.74; H, 4.32; N, 21.90; S, 7.16 Anal. Calcd. for $C_9H_{13}N_7S.2HCl.H_2O$: C, 31.58; H, 5.01; N, 28.64; S, 9.37. Found: C, 31.20; H, 5.22; N, 27.86; S, 8.91 |
| y | $C_2H_5(CH_3)N$ | 61% | >275° | Anal. Calcd. for $C_{10}H_{15}N_7S.2HCl.H_2O$: C, 33.71; H, 5.38; N, 27.52; S, 9.00. Found: C, 33.92; H, 4.90; N, 27.45; S, 9.19 |
| z | $(C_2H_5)_2N$ | 61% | >275° | Anal. Calcd. for $C_{11}H_{17}N_7S.2HCl$: C, 37.50; H, 5.44; N, 27.83; S, 9.10. Found: C, 37.37; H, 5.41; N, 26.43; S, 8.80 |
| aa | morpholino | 45% | >270° | Anal. Calcd. for $C_{11}H_{15}N_7SO.2HCl$: C, 36.07; H, 4.68; N, 26.77; S, 8.75. Found: C, 35.97; H, 5.06; N, 25.95; S, 8.62 |
| bb | pyrrolidino | 68% | >280° | Anal. Calcd. for $C_{11}H_{15}N_7S.2HCl.\frac{1}{2}H_2O$: C, 36.77; H, 5.05; N, 27.29; S, 8.92. Found: C, 37.14; H, 4.98; N, 27.02; S, 8.38 |
| cc | piperidino | 38% | >250° | Anal. Calcd. for $C_{12}H_{17}N_7S.2HCl.\frac{1}{2}H_2O$: C, 38.61; H, 5.40; N, 26.27; S, 8.59. Found: C, 38.67; H, 5.32; N, 26.05; S, 8.71 |
| dd | $C_6H_5(CH_2)_5NH$** | | >250° | Anal. Calcd. for $C_{18}H_{23}N_7S.HBr.HCl$: C, 44.40; H, 5.18; N, 20.14; S, 6.59. Found: C, 44.00; H, 4.97; N, 19.73; S, 6.51. |

*Yield of dihydrochloride over Example 4/Example 5 processes.
**Prepared in the same manner from $C_6H_5(CH_2)_5NH_2$ via the general procedures of Examples 2-5.

By the same sequential procedures of Examples 2–5, 2-aminoheptane, 2-methyl-1-aminocyclohexane, N-ethyl-2-phenyl-2-propylamine, 2-(3-pyridyl)-2-propylamine, N-methyl-1-(p-methylphenyl)ethylamine, N-methyl-1-(o-methoxyphenyl)-2-propylamine, 2-(p-bromophenyl)ethylamine, 2-(p-fluorophenyl)ethylamine, m-fluorobenzylamine, 2,4-dichlorobenzylamine and N-methyl-1-(m-trifluoromethylphenyl)-1-propylamine (prepared by reactive amination of m-trifluoromethylpropiophenone) are converted to the corresponding 2-guanidino-4-(2-substituted-amino-4-imidazolyl)-thiazole dihydrochlorides.

EXAMPLE 6

Gastric Acid Antisecretory Activity

The gastric acid antisecretory activity of compounds of the present invention was determined in overnight fasted, conscious Heidenhain pouch dogs. Pentagastrin (Pentavolon-Ayerst) was used to stimulate acid output by continuous infusion into a superficial leg vein at doses earlier determined to stimulate near maximal acid output from the gastric pouch. Gastric juice was collected at 30 minute intervals following the start of a pentagastrin infusion and measured to the nearest 0.1 ml. Ten collections were taken for each dog during an experiment. Acid concentration was determined by tritrating 1.0 ml of gastric juice to pH 7.4 with 0.1 N sodium hydroxide using an Autoburette and a glass electrode pH meter (Radiometer).

Drug or vehicle was given intravenously 90 minutes following the start of the pentagastrin infusion, at a dose of 1 mg/kg or less. Gastric acid antisecretory effects were calculated by comparing the lowest acid output after drug administration with the mean acid output immediately before drug.

The Example 5 products a to h, n r and cc, at a dose of 1 mg/kg, inhibited gastric secretion at least 21%. Preferred products f to h and w inhibited gastric secretion at least 97% of the same or a lower dose. At a dose of 3 microg/kg, compound n gave 42% inhibition. At 0.1 mg/kg, compound cc gave 72% inhibition.

EXAMPLE 7

Histamine-$H_2$ Antagonist Activity

The histamine-$H_2$ antagonist activity of compounds of the present invention was determined by the following procedure:

Guinea pigs are killed rapidly with a blow to the head, the heart removed and the right atria dissected free. Atria are suspended, isometrically, in a temperature-controlled (32°±2°) tissue bath (10 ml) containing oxygenated (95% $O_2$; 5% $CO_2$) Krebs-Henseleit buffer (pH 7.4) and are allowed to stabilize approximately one hour during which time the tissue bath is flushed several times. Individual atrial contractions are followed with a force-displacement transducer connected to a cardiotachometer and Grass polygraph recorder. After obtaining a dose-response curve to histamine, the bath containing each atrium is flushed several times with fresh buffer and the atria reequilibrated to basal rates. Following the return to basal rate, test compounds are addded at selected final concentrations and the histamine dose-response curve is again determined in the presence of antagonist. Results are expressed as dose-ratios, the ratio of histamine concentrations required to produce one-half of maximal stimulation in the presence and absence of antagonist, and the apparent dissociation constant of the $H_2$-receptor antagonist $pA_2$, is determined.

The Example 5 products a to l, n, o and q to bb gave $pA_2$ values of at least 5.9. Preferred products f to i, n, s, t and w gave $pA_2$ of 7.0 or greater. The highest value (8.8) was obtained with product n.

EXAMPLE 8

Inhibition of Ethanol-Induced Ulceration in Rats

The antiulcer activity of the products of this invention was also determined by an ethanol-induced rat ulcer assay. In this test, overnight fasted male rats are given drug (5 mg/kg) or water orally fifteen minutes prior to an orally administered dose of absolute ethanol (1.0 ml). One hour after the ethanol challenge the animals (8/group) are killed and the stomachs examined for the presence of lesions. After sacrifice the abdomen is opened and a locking hemostat placed at the pylorus. Six ml of a 4% solution of formaldehyde was injected into the stomach with a gastric feeding tube and a second locking hemostat was used to seal the esophagus. The stomach was removed, opened along the greater curvature and examined for ulceration.

The scoring system used to quantitate the ethanol-induced lesions is given below.

| Score | Ulcer Score Table Definition |
| --- | --- |
| 1 | Normal appearing stomach |
| 2 | Pinpoint sized lesions |
| 3 | Lesions, 2 or fewer; pinpoint lesions may be present |
| 4 | Lesions, >2; pinpoint lesions may be present |
| 5 | Lesions with hemorrhage |

For each group of animals an ulcer index is calculated as follows:

Ulceration Index=(the sum of the scores of the group)×(the sum of the number of ulcers in the group)×(the fraction of the group having any incidence of ulceration).

The percentage inhibition of ulcers is calculated as follows:

% Inhibition=100×[(ulcer index controls)−(ulcer index drug-treated)]÷(ulcer index controls).

At an oral dose of 30 mg/kg, Example 5 products a to k, m, r to u, w, y, z, bb and cc showed at least 19% inhibition of ethanol-induced ulceration. At the same dosage, compounds o, v, x and aa demonstrated no significant activity, compounds n, p and q showed 7–13% inhibition, compounds u and cc showed 21–51% inhibition, and preferred compounds f to i, s, t and w showed 86–100% inhibition.

We claim:

1. A compound of the formula

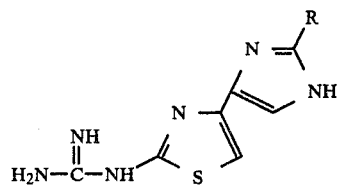

wherein
R is $NHR^1$ or $NR^2R^3$;
$R^1$ is $(C_7-C_{12})$alkyl, $(C_6-C_{11})$pyridylalkyl or $(C_{11}-C_{12})$phenylalkyl, optionally monosubstituted or disubstituted on the phenyl group with chloro, bromo, fluoro, $(C_1-C_3)$alkoxy or trifluoromethyl; and
$R^2$ and $R^3$ are each independently $(C_1-C_{12})$alkyl or $(C_7-C_{12})$phenylalkyl, optionally monosubstituted or disubstituted on the phenyl group with chloro, bromo, fluoro, $(C_1-C_3)$alkyl, $(C_1-C_3)$alkoxy or trifluoromethyl; or
$R^2$ and $R^3$ are taken together with the nitrogen to which they are attached to form a pyrrolidone, piperidine, perhydro-1H-azepine, or morpholine ring;
or a pharmaceutically-acceptable acid addition salt thereof.

2. A compound of claim 1 wherein R is $NHR^1$ and $R^1$ is $(C_7-C_{12})$alkyl.

3. The compound of claim 2 wherein $R^1$ is n-heptyl.

4. The compound of claim 2 wherein $R^1$ is n-octyl.

5. The compound of claim 2 wherein $R^1$ is n-nonyl.

6. A compound of claim 1 wherein R is $NHR^1$ and $R^1$ is $(C_6-C_{11})$pyridylalkyl.

7. The compound of claim 6 wherein $R^1$ is 2-(2-pyridyl)-1-ethyl.

8. A compound of claim 1 wherein R is $NHR^1$ and $R^1$ is $(C_{11}-C_{12})$phenylalkyl, optionally substituted on the phenyl ring.

9. The compound of claim 1 wherein $R^1$ is 5-phenyl-1-pentyl.

10. A compound of claim 1 wherein R is $NR^2R^3$.

11. The compound of claim 12 wherein $R^2$ and $R^3$ are taken together with the nitrogen to which they are attached to form a piperidine ring.

12. A pharmaceutical composition for the inhibition of gastric ulcers in a mammal which comprises an inert carrier and a gastric ulcer inhibiting amount of a compound of claim 1.

13. A method of inhibiting gastric ulcers in a mammal which comprises administering to said mammal a gastric ulcer inhibiting amount of a compound of claim 1.

14. A process for the preparation of a compound of the formula

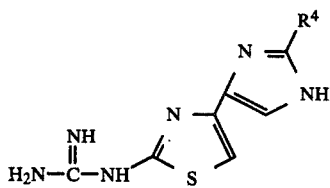

wherein
$R^4$ is $NHR^5$ or $NR^2R^3$;
$R^5$ is $(C_1-C_{12})$alkyl, $(C_3-C_8)$cycloalkyl, $(C_6-C_{11})$pyridylalkyl or $(C_7-C_{12})$phenylalkyl, optionally monosubstituted or disubstituted on the phenyl group with chloro, bromo, fluoro, $(C_1-C_3)$alkyl, $(C_1-C_3)$alkoxy or trifluoromethyl; and
$R^2$ and $R^3$ are each independently $(C_1-C_{12})$alkyl or $(C_7-C_{12})$phenylalkyl, optionally monosubstituted or disubstituted on the phenyl group with chloro, bromo, fluoro, $(C_1-C_3)$alkyl, $(C_1-C_3)$alkoxy or trifluoromethyl; or
$R^2$ and $R^3$ are taken together with the nitrogen to which they are attached to form a pyrrolidine, piperidine, perhydro-1H-azepine, or morpholine ring;
which comprises the steps of:
(a) reacting the oxazole of the formula

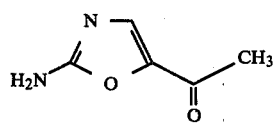

with an excess of an amine of the formula $H_2NR^5$ or $HNR^2R^3$, wherein $R^2$, $R^3$ and $R^5$ are as defined above, in an aqueous solvent, to form a 5-acetylimidazole of the formula

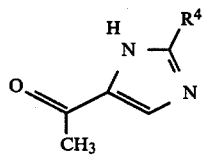

wherein $R^4$ is as defined above;
(b) brominating the imidazole of the formula (II) under acidic conditions to form a bromoacetylimidazole of the formula

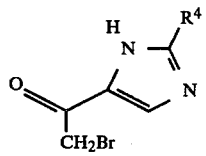

wherein $R^4$ is as defined above; and
(c) coupling the bromoacetylimidazole of the formula (III) with a compound of the formula

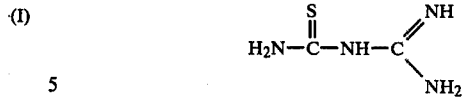

to form the compound of the formula (I).
15. A process of claim 14 wherein $R^4$ is $NHR^5$ and $R^5$ is $(C_3-C_8)$cycloalkyl.
16. A process of claim 15 wherein $R^5$ is cyclopropyl.
17. A process of claim 14 wherein $R^4$ is $NHR^5$ and $R^5$ is $(C_1-C_{12})$alkyl.
18. The process of claim 17 wherein $R^5$ is n-hexyl.
19. The process of claim 17 wherein $R^5$ is n-heptyl.
20. The process of claim 17 wherein $R^5$ is n-octyl.
21. The process of claim 17 wherein $R^5$ is n-nonyl.
22. A process of claim 14 wherein $R^4$ is $NHR^5$ and $R^5$ is $(C_6-C_{11})$pyridylalkyl.
23. The process of claim 22 wherein $R^5$ is 2-(2-pyridyl)-1-ethyl.
24. A process of claim 14 wherein $R^4$ is $NHR^5$ and $R^5$ is $(C_7-C_{12})$phenylalkyl, optionally substituted on the phenyl ring.
25. The process of claim 24 wherein $R^5$ is 2-(p-chlorophenyl)-1-ethyl.
26. The process of claim 24 wherein $R^5$ is 3-phenyl-1-propyl.
27. The process of claim 24 wherein $R^5$ is 4-phenyl-1-butyl.
28. The process of claim 24 wherein $R^5$ is 5-phenyl-1-pentyl.
29. A process of claim 14 wherein $R^4$ is $NR^2R^3$.
30. The process of claim 29 wherein $R^2$ and $R^3$ are taken together with the nitrogen to which they are attached to form a piperidine ring.
31. A process of claim 14 which further comprises isolation of the compound of the formula (I) as a crystalline hydrobromide salt.
32. A crystalline salt of the formula

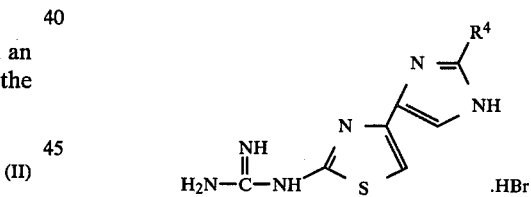

wherein
$R^4$ is $NHR^5$ or $NR^2R^3$;
$R^5$ is $(C_1-C_{12})$alkyl, $(C_3-C_8)$cycloalkyl, $(C_6-C_{11})$pyridylalkyl or $(C_7-C_{12})$phenylalkyl, optionally monosubstituted or disubstituted on the phenyl group with chloro, bromo, fluoro, $(C_1-C_3)$alkyl, $(C_1-C_3)$alkoxy or trifluoromethyl; and
$R^2$ and $R^3$ are each indpendently $(C_1-C_{12})$alkyl or $(C_7-C_{12})$phenylalkyl, optionally monosubstituted or disubstituted on the phenyl group with chloro, bromo, fluoro, $(C_1-C_3)$alkyl, $(C_1-C_3)$alkoxy or trifluoromethyl; or
$R^2$ and $R^3$ are taken together with the nitrogen to which they are attached to form a pyrrolidine, piperidine, perhydro-1H-azepine, or morpholine ring.
33. A salt of claim 32 wherein $R^4$ is $NHR^5$.
34. A salt of claim 33 wherein $R^5$ is $(C_1-C_{12})$alkyl.
35. A salt of claim 34 wherein $R^5$ is n-hexyl.
36. A salt of claim 34 wherein $R^5$ is n-heptyl.

* * * * *